United States Patent
Shen et al.

(10) Patent No.: US 7,379,576 B2
(45) Date of Patent: May 27, 2008

(54) METHOD AND SYSTEM FOR PATIENT IDENTIFICATION IN 3D DIGITAL MEDICAL IMAGES

(75) Inventors: Hong Shen, Princeton, NJ (US); Benjamin Odry, West New York, NJ (US); Shuping Qing, Princeton, NJ (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 637 days.

(21) Appl. No.: 10/974,313

(22) Filed: Oct. 27, 2004

(65) Prior Publication Data

US 2005/0111714 A1    May 26, 2005

Related U.S. Application Data

(60) Provisional application No. 60/516,955, filed on Nov. 3, 2003.

(51) Int. Cl.
*G06K 9/00* (2006.01)
(52) U.S. Cl. ................ 382/131; 382/128; 378/4; 378/21; 378/901
(58) Field of Classification Search ........ 382/128, 382/129, 130, 131, 132, 133, 134, 164, 171, 382/173, 306; 600/134, 410, 415, 425; 378/4, 378/21, 23, 24, 25, 26, 27, 28, 901; 128/846, 128/905, 908, 923
See application file for complete search history.

(56) References Cited

U.S. PATENT DOCUMENTS

| 5,782,762 | A * | 7/1998 | Vining | 600/407 |
| 5,935,060 | A * | 8/1999 | Iliff | 600/300 |
| 6,364,845 | B1 * | 4/2002 | Duffy et al. | 600/558 |
| 7,024,027 | B1 * | 4/2006 | Suri et al. | 382/130 |

\* cited by examiner

*Primary Examiner*—Abolfazl Tabatabai

(57) ABSTRACT

A method of identifying a patient from digital medical images includes providing a first digital image volume of an organ of a patient and a second digital image volume of the same organ, segmenting each slice of the first image volume and calculating a cross-sectional area of the organ in each slice to form a first area profile, segmenting each slice of the second image volume and calculating a cross-sectional area of the organ in each slice to form a second area profile, and comparing the first area profile with the second area profile to determine a correlation value for the two profiles. Based on the correlation value between the first area profile and the second area profile, it is determined whether the first digital image volume of the organ and the second digital image volume of the same organ came from the same patient.

19 Claims, 4 Drawing Sheets

| | Panel 1 | | Panel 2 | | Panel 3 | |
|---|---|---|---|---|---|---|
| | A1 | A2 | A1 | A2 | A1 | A2 |
| Total case | 30 | 960 | 30 | 991 | 31 | 1051 |
| Success /Failure | 29/1 | 907/53 | 29/1 | 932/59 | 31/2 | 985/66 |
| Success rate /Failure rate | 96.66% /3.3% | 94.48% /5.52% | 96.67% /3.33% | 94.05% /5.95% | 93.55% / 6.45 | 93.72% / 6.28% |

METHOD AND SYSTEM FOR PATIENT IDENTIFICATION IN 3D DIGITAL MEDICAL IMAGES

CROSS REFERENCE TO RELATED UNITED STATES APPLICATIONS

This application claims priority from "PATIENT IDENTIFICATION IN 3D DIGITAL MEDICAL IMAGES", U.S. Provisional Application No. 60/516,955 of Shen, et al., filed Nov. 3, 2003, the contents of which are incorporated herein by reference.

TECHNICAL FIELD

This invention is directed to the automatic extraction of anatomic features from 3D digital medical images for patient identification.

DISCUSSION OF THE RELATED ART

Computerized medical equipment, such as computerized tomography (CT) scanners and magnetic resonance imaging (MRI) machines, has been widely used in the screening and diagnosis of many diseases in all human body parts. For example, lung cancer screening and diagnosis is one such application for CT scanners.

In many cases, it is desirable to be able to identify the patient from the data itself, without resorting to patient records and names, which could be unreliable and erroneous. On the other hand, this advanced equipment produces large volumes of high quality data from which one can extract distinct anatomic information that may be unique enough to identify patients.

For example, in a chest CT follow-up, two CT volume scans at different times of the same patient are loaded, so the physician can observe the development of a certain disease over a period of time. Associated with the volume data are two tags to identify a patient: Patient Name and Patient ID, where the name is one tag that contains surname and all given names. Those two tags appear to be not very reliable. It happens often that the patient name does not match because of mistyping. Sometimes there are only surnames, or there are redundant characters between surname and given name, etc. One solution could be to force the radiologist to correct the tag name using a "correct-and-rearrange" functionality but this would be an additional step in the physician workflow. The Patient ID can also be different if the patient was registered twice.

Currently, there is no scheme for automatic patient identification. For a CT follow-up study, it is solely dependent on the users to make sure one loads in two data sets from the same patient. Obviously, this could be error prone. If the user mistakenly loaded two data sets from two different patients, the conclusion of diagnosis will be completely irrelevant and wrong.

SUMMARY OF THE INVENTION

Herein disclosed are methods to automatically determine whether the two loaded data sets belong to the same patient, using only anatomic information, rather than foreign information such as patient names and id's. These methods can automatically extract anatomic features that are most distinctive from the volume data itself, eliminating the possibility of attaching wrong names to data. This can be used by itself or in combination with patient information to make the decisions highly reliable and robust. The methods can be applied to datasets of cross-modality, such as CT-MRI, if the extracted anatomic features are invariant among modalities.

In one aspect of the invention, there is provided a method of identifying a patient from digital medical images. The method comprises the steps of providing a first digital image volume of an organ of a patient and a second digital image volume of the same organ from a patient, wherein each said image comprises a plurality of intensities corresponding to a domain of points in a D-dimensional space; segmenting each slice of the first image volume and calculating a cross-sectional area of the organ in each slice to form a first area profile of the first image volume; segmenting each slice of the second image volume and calculating a cross-sectional area of the organ in each slice to form a second area profile of the second image volume; and comparing the first area profile with the second area profile to determine a correlation value for the two profiles. Based on the correlation value between the first area profile and the second area profile, it is determined whether the first digital image volume of the organ and the second digital image volume of the same organ came from the same patient.

In a further aspect of the invention, the organ is the lungs, and the first and second image volumes are computerized tomography (CT) images. The slice can be an axial slice, a coronal slice, or a sagittal slice. The method can further include calculating a cross-sectional area of the organ in each axial slice, each coronal slice, and each sagittal slice of the first image volume to form a first axial area profile, first coronal area profile, and first sagittal area profile; calculating a cross-sectional area of the organ in each axial slice, each coronal slice, and each sagittal slice of the second image volume to form a second axial area profile, second coronal area profile, and second sagittal area profile. Each of the first area profiles is compared to the corresponding second area profile to determine an axial correlation value, a coronal correlation value, and a sagittal correlation value to determine whether the first digital image volume of the organ and the second digital image volume of the same organ came from the same patient, based on the correlation values between the first area profiles and the second area profiles.

In a further aspect of the invention, one of the first area profile and the second area profile is shifted and scaled before being compared to the other area profile, and a correlation value is determined for the shift and scale value. A maximum correlation value between the first and second area profiles is determined from a plurality of shift and scale values, wherein the maximum correlation value is taken as the correlation value between the first and second area profiles.

In a further aspect of the invention, the determination of whether the first digital image volume of the organ and the second digital image volume of the same organ come from the same patient is based on the Bayesian classification rule
If $$\frac{P(C \mid A_1)}{P(C \mid A_2)} > \frac{P(A_2)}{P(A_1)}$$

decide as $A_1$, else decide as $A_2$, where $P(C|A_i)$ is the probability distribution function of correlation value C for class $A_i$, $P(A_i)$ is the a priori probability of class A, and where $A_1$ is the class of same-patient image pairs and $A_2$ is the class of different-patient image pairs.

In a further aspect of the invention, if the probability of loading two image volumes of the same patient equals that of different patients, the determination is based on the rule If $P(C|A_1) > P(C|A_2)$ decide as $A_1$, else decide as $A_2$.

In another aspect of the invention, there is provided a program storage device readable by a computer, tangibly embodying a program of instructions executable by the computer to perform the method steps for identifying patients from digital medical images.

DETAILED DESCRIPTION OF THE PREFERRED EMBODIMENTS

Three-dimensional digital medical images are usually generated by computerized medical equipment such as CT scanners and MRI machines. Selected anatomic information and structures can be extracted as features from this type of volume data. These features, if unique enough, can be used to identify the patient. The anatomic information and structures to be extracted to be features for identification should be reliable and stable. For instance, they should be relatively immune to segmentation errors, body pose, and inhalation levels. This will enable the correct identification under most conditions.

Figure 1:
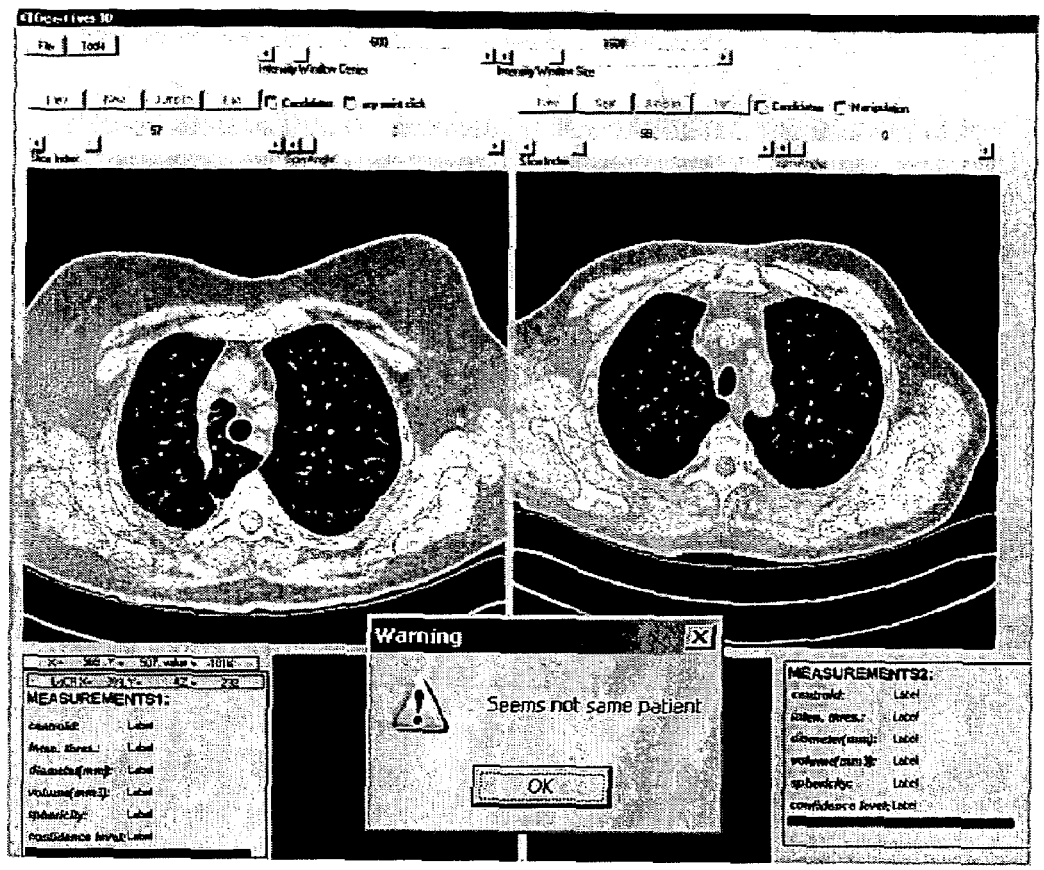
FIG. 1 depicts a pair of chest CT data sets wherein the system determined that the two data sets do not belong to the same patient.

The methods and systems disclosed herein can be used to identify individuals using biological traits. The software application and algorithm disclosed herein can employ 2-D and 3-D renderings and images of an organ or organ system. As an example, two loaded datasets in a chest CT follow-up study are compared to determine if in fact they belong to the same patient, as shown in FIG. 1. However, it should be understood that the methods can be applied to analyzing images formed using other modalities, such as MRI, RET, or x-ray, and of other organs as is known to those skilled in the art.

Figure 2:
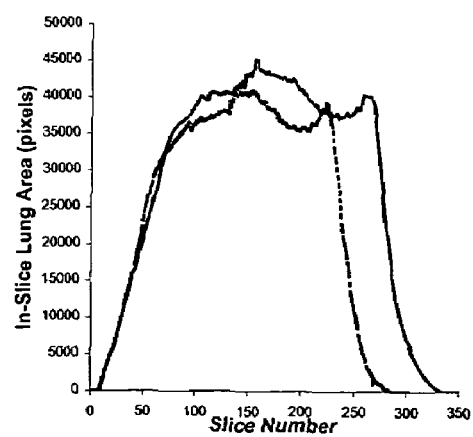
FIG. 2 depicts a plot of lung area with respect to slice number.
Figure 5:
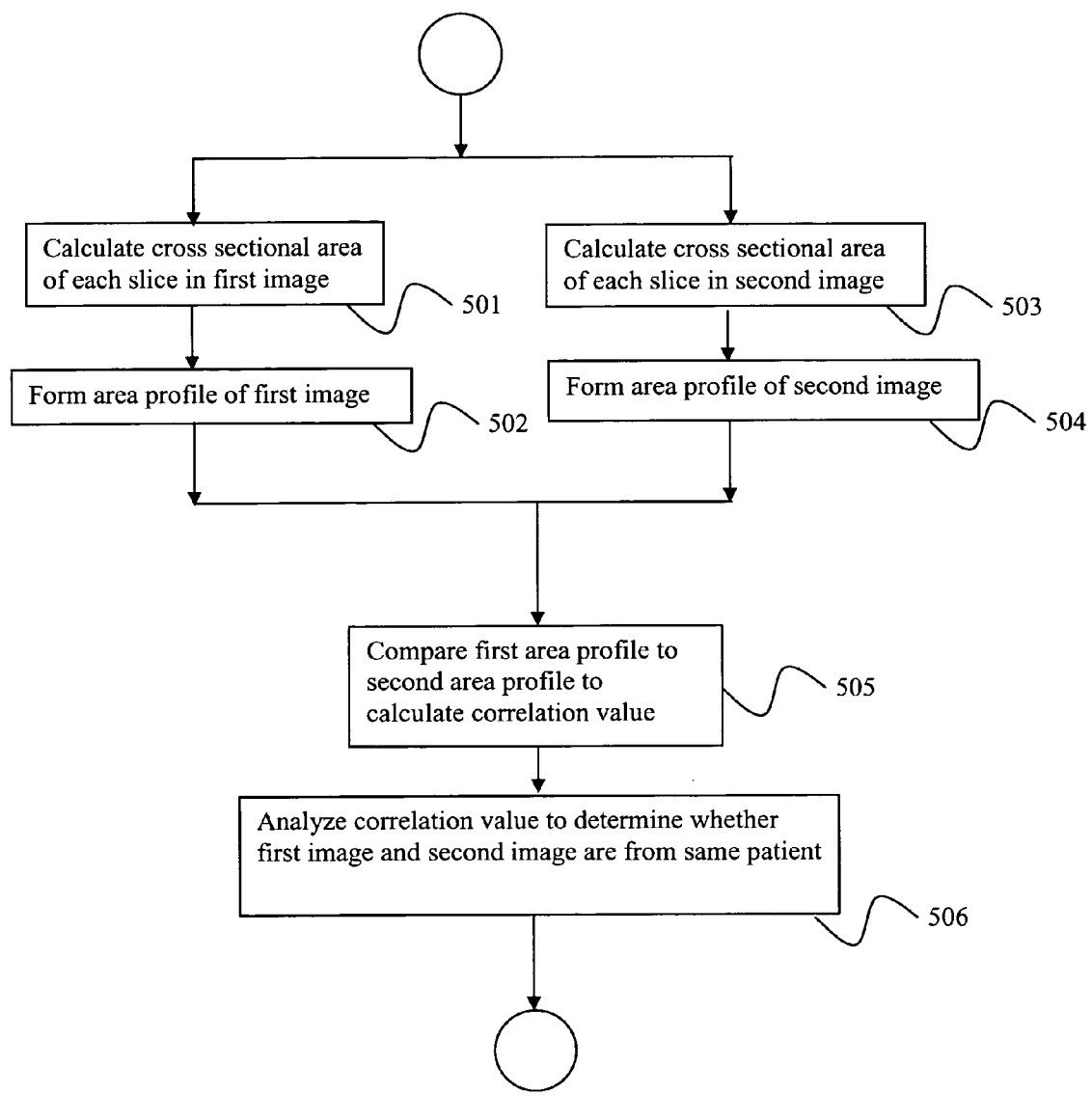
FIG. 5 depicts a flow chart of a preferred method of the invention.

Referring now to the flowchart depicted in FIG. 5, two sets of lung regions are segmented for each axial slice in the volume data. The areas of the left and right lungs are computed in each set at steps 501, 503, to obtain two arrays of area profiles at steps 502 and 504, for the left lung and right lung, respectively. Typically, a lung slice is 512×512 pixels, for a total image size of over 260,000 pixels. The lung area value for each axial slice can be stored in an array. These two area profile arrays reflect the variation of lung areas across the axial slices, as shown in FIG. 2. Here, the two curves on each graph represent two scans of the same patient at different times. The left and right graphs display the lung area curves for the left and right lung areas, respectively. If the two data sets belong to the same patient, the lung area variations should have high correlation values.

The correlation values between the area profiles of the two data sets are then computed at step 505 as features for patient identification. The correlation value between two curves depends on the how the two curves are aligned. Since there are usually scaling and shift factors between the slice numbers of the two data sets, one needs to search for the maximum correlation value. One of the two curves is scaled and shifted to align with the other curve. For each scale and shift value, one computes the correlations and searches for the scale and shift that achieve the maximum correlation, which is then used as the extracted feature value.

Similarly, the area arrays and their corresponding correlations can be computed for coronal and sagittal slices. There will thus be a total of 6 possible correlation values for comparing lung images.

The correlation of the area profiles is apparently independent of body pose. It is also invariant when inhalation level changes, since one uses not the absolute value of the areas, but only the variation trend of the areas across the slices, which independent of the inhalation if every part of the lung expands or shrinks uniformly. The area profile correlations are also relatively immune to segmentation errors, and a small error in some slices will not change the correlation results. For example, an entire slice can be dropped from a profile calculation without effecting the profile correlation, and the profile correlation can tolerate a lung slice error of up to 25%, or about 60,000 pixels.

After the profile correlations are calculated, the correlation values are analyzed at step 506 to determine if they represent a same-patient pair or not. These 6 feature values can be used either individually, or a median or average of the correlation values can be used as features for classification. Other statistics, as are known to those skilled in the art, can also be computed from these area arrays. The choice of methods can be decided from the experiments.

Figures 3, 4:
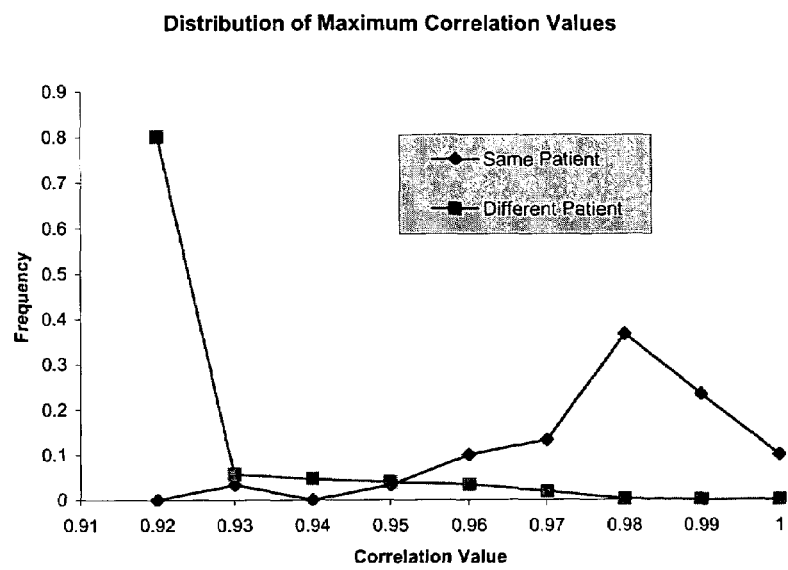
FIG. 3 depicts the different distribution of correlation values between two classes.
FIG. 4 depicts a table showing the success rates of same-patient and different-patient decisions.

Shown in FIG. 3 is the distribution of maximum correlation values for same-patient (class $A_1$) and different-patient (class $A_2$) pairs. The y axis shows the normalized histogram (frequency) values. The two distributions are well separated, but there will some overlap. The Bayesian classification rule gives If $$\frac{P(C|A_1)}{P(C|A_2)} > \frac{P(A_2)}{P(A_1)}$$

decide as $A_1$, else decide as $A_2$, where $P(C|A_i)$ is the probability distribution function (pdf) of correlation value C for class $A_i$. One example of a pdf derived form experimental data is shown in FIG. 3. $P(A_i)$ is the a priori probability of class A, and it needs to be estimated before determining the classification boundary. If it can be assumed that the probability of loading the two data sets of the same patient equals that of different patient, then the following holds:

If $P(C|A_1) > P(C|A_2)$ decide as $A_1$, else decide as $A_2$.

This is the maximum likelihood classification. However, it is less likely for a physician to load two datasets that belong to different patients. Furthermore, there could be a classification error, and one needs to decide which error is more damaging—classifying class $A_1$ into class $A_2$, or the reverse. This is purely a decision on application context and can be subjective.

In experiments presented herein, 3 panels of datasets were used, built from 45 previously existing datasets. The datasets concern 20 screening patients with one or two follow up studies. Each panel contains 2 groups ($A_1$ and $A_2$) as previously described. All datasets come from a Siemens Multi-slice helical CT Scanner, with a 1.0 mm collimator and reconstructed in 1.25 mm or 1.0 mm increments at 1.0 mm intervals and were obtained from the lung apices through the adrenal glands.

First, a training panel (Panel 1) is used to determine the correlation boundary as 0.95. Then 31 pairs are added to the second group (Panel 2) and finally 60 pairs are added to the second group from Panel 2 and 1 pair to the first group (Panel 3).

The success rates of classification are shown in FIG. 4. As can be seen, for each of the 3 panels, images from the A1 group were correctly determined to be from the same patient 96.66%, 96.67%, and 93.55% for, respectively, Panel 1, Panel 2, and Panel 3. Similarly, images from the A2 group were correctly determined to be from different patients 94.48%, 94.05%, and 93.72% for respectively, Panel 1, Panel 2, and Panel 3.

It is to be understood that the present invention can be implemented in various forms of hardware, software, firmware, special purpose processes, or a combination thereof. In one embodiment, the present invention can be implemented in software as an application program tangible embodied on a computer readable program storage device. The application program can be uploaded to, and executed by, a machine comprising any suitable architecture.

Figure 6:
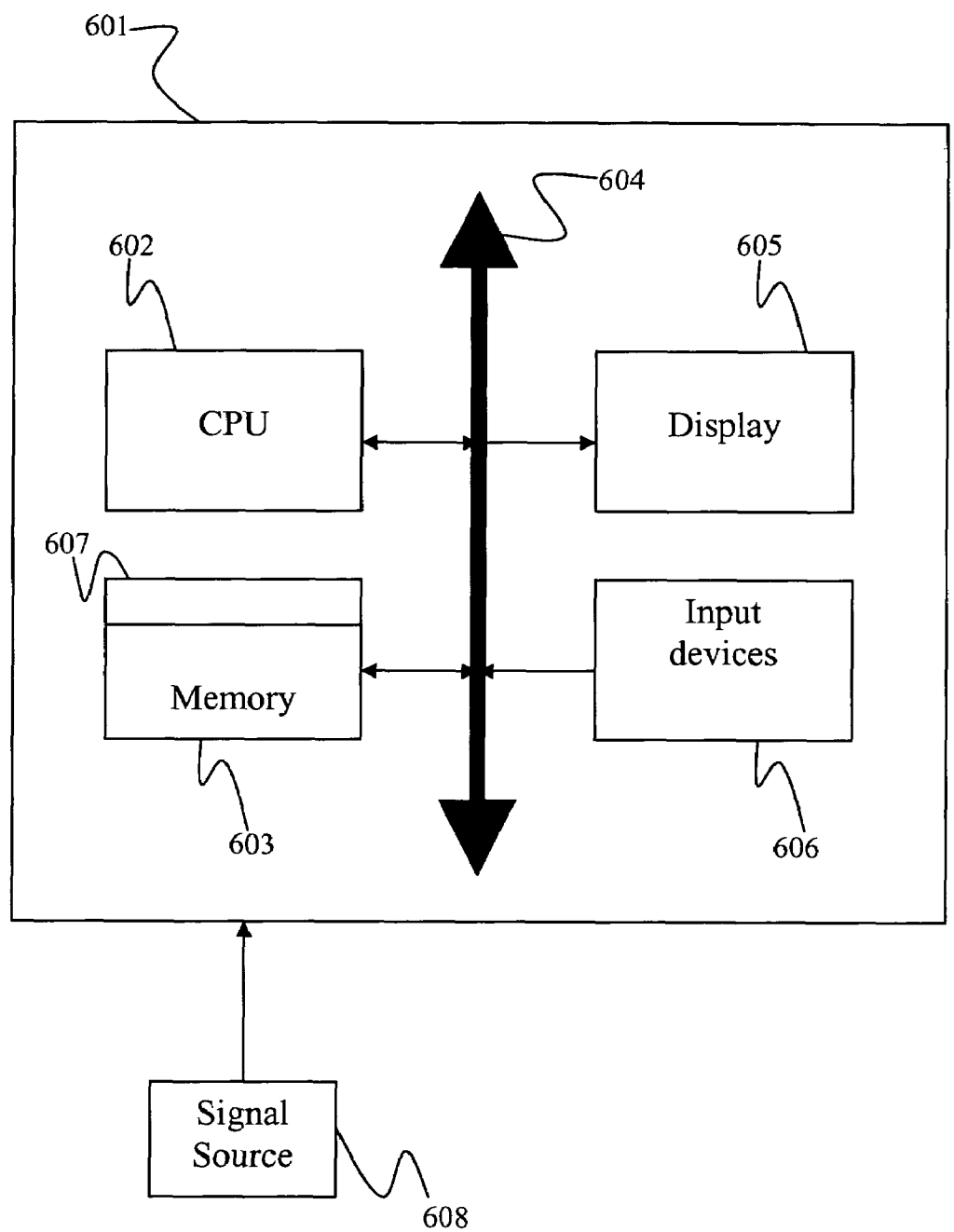
FIG. 6 depicts an exemplary computer system for implementing a preferred embodiment of the invention.

Referring now to FIG. 6, according to an embodiment of the present invention, a computer system 601 for implementing the present invention can comprise, inter alia, a central processing unit (CPU) 602, a memory 603 and an input/output (I/O) interface 604. The computer system 601 is generally coupled through the I/O interface 604 to a display 605 and various input devices 606 such as a mouse and a keyboard. The support circuits can include circuits such as cache, power supplies, clock circuits, and a communication bus. The memory 603 can include random access memory (RAM), read only memory (ROM), disk drive, tape drive, etc., or a combinations thereof. The present invention can be implemented as a routine 607 that is stored in memory 603 and executed by the CPU 602 to process the signal from the signal source 608. As such, the computer system 601 is a general purpose computer system that becomes a specific purpose computer system when executing the routine 607 of the present invention.

The computer system 601 also includes an operating system and micro instruction code. The various processes and functions described herein can either be part of the micro instruction code or part of the application program (or combination thereof) which is executed via the operating system. In addition, various other peripheral devices can be connected to the computer platform such as an additional data storage device and a printing device.

It is to be further understood that, because some of the constituent system components and method steps depicted in the accompanying figures can be implemented in software, the actual connections between the systems components (or the process steps) may differ depending upon the manner in which the present invention is programmed. Given the teachings of the present invention provided herein, one of ordinary skill in the related art will be able to contemplate these and similar implementations or configurations of the present invention.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed is:

1. A method of identifying a patient from digital medical images, said method comprising the steps of:
providing a first digital image volume of an organ of a patient and a second digital image volume of the same organ from a patient, wherein each said image comprises a plurality of intensities corresponding to a domain of points in a D-dimensional space;
segmenting each slice of the first image volume and calculating a cross-sectional area of the organ in each slice to form a first area profile of the first image volume;
segmenting each slice of the second image volume and calculating a cross-sectional area of the organ in each slice to form a second area profile of the second image volume;
comparing the first area profile with the second area profile to determine a correlation value for the two profiles;
determining, based on the correlation value between the first area profile and the second area profile, whether the first digital image volume of the organ and the second digital image volume of the same organ came from the same patient, wherein the determination of whether the first digital image volume of the organ and the second digital image volume of the same organ come from the same patient is based on the Bayesian classification rule
If $$\frac{P(C|A_1)}{P(C|A_2)} > \frac{P(A_2)}{P(A_1)}$$

decide as $A_1$, else decide as $A_2$,
where $P(C|A_i)$ is the probability distribution function of correlation value C for class $A_i$, $P(A_i)$ is the a priori probability of class A, and where $A_1$ is the class of same-patient image pairs and $A_2$ is the class of different-patient image pairs.

2. The method of claim 1, wherein the organ is the lungs, and the first and second image volumes are computerized tomography (CT) images.

3. The method of claim 2, wherein the slice can be an axial slice, a coronal slice, or a sagittal slice.

4. The method of claim 3, further comprising the steps of:
calculating a cross-sectional area of the organ in each axial slice, each coronal slice, and each sagittal slice of the first image volume to form a first axial area profile, first coronal area profile, and first sagittal area profile;
calculating a cross-sectional area of the organ in each axial slice, each coronal slice, and each sagittal slice of the second image volume to form a second axial area profile, second coronal area profile, and second sagittal area profile;

comparing each of the first area profiles to the corresponding second area profile to determine an axial correlation value, a coronal correlation value, and a sagittal correlation value; and determining whether the first digital image volume of the organ and the second digital image volume of the same organ came from the same patient, based on the correlation values between the first area profiles and the second area profiles.

5. The method of claim 1, wherein one of the first area profile and the second area profile is shifted and scaled before being compared to the other area profile, and wherein a correlation value is determined for the shift and scale value.

6. The method of claim 5, wherein a maximum correlation value between the first and second area profiles is determined from a plurality of shift and scale values, wherein the maximum correlation value is taken as the correlation value between the first and second area profiles.

7. The method of claim 1, wherein, if the probability of loading two image volumes of the same patient equals that of different patients, the determination is based on the rule If $P(C|A_1) > P(C|A_2)$ decide as $A_1$, else decide as $A_2$.

8. A computer readable program storage device tangibly embodying a program of instructions executable by a computer to perform the method steps for identifying patients from digital medical images, said method comprising the steps of:

providing a first digital image volume of an organ of a patient and a second digital image volume of the same organ from a patient, wherein each said image comprises a plurality of intensities corresponding to a domain of points in a D-dimensional space;

segmenting each slice of the first image volume and calculating a cross-sectional area of the organ in each slice to form a first area profile of the first image volume;

segmenting each slice of the second image volume and calculating a cross-sectional area of the organ in each slice to form a second area profile of the second image volume;

comparing the first area profile with the second area profile to determine a correlation value for the two profiles;

determining, based on the correlation value between the first area profile and the second area profile, whether the first digital image volume of the organ and the second digital image volume of the same organ came from the same patient, wherein the determination of whether the first digital image volume of the organ and the second digital image volume of the same organ come from the same patient is based on the Bayesian classification rule If $$\frac{P(C|A_1)}{P(C|A_2)} > \frac{P(A_2)}{P(A_1)}$$

decide as $A_1$, else decide as $A_2$,
where $P(C|A_i)$ is the probability distribution function of correlation value C for class $A_i$, $P(A_i)$ is the a priori probability of class A, and where $A_1$ is the class of same-patient image pairs and $A_2$ is the class of different-patient image pairs.

9. The computer readable program storage device of claim 8, wherein the organ is the lungs, and the first and second image volumes are computerized tomography (CT) images.

10. The computer readable program storage device of claim 9, wherein the slice can be an axial slice, a coronal slice, or a sagittal slice.

11. The computer readable program storage device of claim 10, the method steps further comprising:

calculating a cross-sectional area of the organ in each axial slice, each coronal slice, and each sagittal slice of the first image volume to form a first axial area profile, first coronal area profile, and first sagittal area profile;

calculating a cross-sectional area of the organ in each axial slice, each coronal slice, and each sagittal slice of the second image volume to form a second axial area profile, second coronal area profile, and second sagittal area profile;

comparing each of the first area profiles to the corresponding second area profile to determine an axial correlation value, a coronal correlation value, and a sagittal correlation value; and determining whether the first digital image volume of the organ and the second digital image volume of the same organ came from the same patient, based on the correlation values between the first area profiles and the second area profiles.

12. The computer readable program storage device of claim 8, the method steps further comprising shifting and scaling one of the first area profile and the second area profile before comparing it to the other area profile, and wherein a correlation value is determined for the shift and scale value.

13. The computer readable program storage device of claim 12, wherein a maximum correlation value between the first and second area profiles is determined from a plurality of shift and scale values, wherein the maximum correlation value is taken as the correlation value between the first and second area profiles.

14. The computer readable program storage device of claim 8, wherein, if the probability of loading two image volumes of the same patient equals that of different patients, the determination is based on the rule If $P(C|A_1) > P(C|A_2)$ decide as $A_1$, else decide as $A_2$.

15. A method of identifying a patient from digital medical images, said method comprising the steps of:

providing a first digital image volume of the lungs of a patient and a second digital image volume of the lungs from a patient, wherein each said image comprises a plurality of intensities corresponding to a domain of points in a D-dimensional space;

segmenting each axial slice of the first image volume and calculating a cross-sectional area of the lungs in each axial slice to form a first axial area profile of the first image volume;

segmenting each axial slice of the second image volume and calculating a cross-sectional area of the lungs in each axial slice to form a second axial area profile of the second image volume;

comparing the first axial area profile with the second axial area profile to determine a correlation value for the two profiles;

determining whether the first digital image volume of the lungs and the second digital image volume of the lungs came from the same patient, based on the Bayesian classification rule If $$\frac{P(C|A_1)}{P(C|A_2)} > \frac{P(A_2)}{P(A_1)}$$

decide as $A_1$, else decide as $A_2$,
where $P(C|A_i)$ is the probability distribution function of correlation value C for class $A_i$, $P(A_i)$ is the a priori probability of class A, and where $A_1$ is the class of same-patient image pairs and $A_2$ is the class of different-patient image pairs.

16. The method of claim 15, further comprising the steps of:
calculating a cross-sectional area of the lungs in each coronal slice and each sagittal slice of the first image volume to form a first coronal area profile and first sagittal area profile;
calculating a cross-sectional area of the lungs in each coronal slice and each sagittal slice of the second image volume to form a second coronal area profile, and second sagittal area profile;
comparing each of the first area profiles to the corresponding second area profile to determine a coronal correlation value and a sagittal correlation value; and
determining whether the first digital image volume of the organ and the second digital image volume of the same organ came from the same patient, based on the correlation values between the first area profiles and the second area profiles.

17. The method of claim 15, wherein one of the first axial area profile and the second axial area profile is shifted and scaled before being compared to the other area profile, and wherein a correlation value is determined for the shift and scale value.

18. The method of claim 17, wherein a maximum correlation value between the first and second area profiles is determined from a plurality of shift and scale values, wherein the maximum correlation value is taken as the correlation value between the first and second area profiles.

19. The method of claim 15, wherein, if the probability of loading two image volumes of the same patient equals that of different patients, the determination is based on the rule If $P(C|A_1) > P(C|A_2)$ decide as $A_1$, else decide as $A_2$.

* * * * *